United States Patent [19]

Bonnet

[11] Patent Number: 5,312,418
[45] Date of Patent: May 17, 1994

[54] INSTRUMENT FOR LITHOTRIPSY

[75] Inventor: Ludwig Bonnet, Knittlingen, Fed. Rep. of Germany

[73] Assignee: Richard Wolf GmbH, A Corporation of the Federal Republic of Germany, Knittlingen, United Kingdom

[21] Appl. No.: 51,043

[22] Filed: Apr. 21, 1993

[30] Foreign Application Priority Data

Apr. 29, 1992 [DE] Fed. Rep. of Germany ....... 4214148

[51] Int. Cl.⁵ .............................. A61B 8/00
[52] U.S. Cl. .................. 606/128; 606/127; 606/1; 128/4; 128/6
[58] Field of Search .............. 128/4, 6; 604/283; 606/1, 127, 128, 108

[56] References Cited

U.S. PATENT DOCUMENTS

| | | | |
|---|---|---|---|
| 4,750,488 | 6/1988 | Wuchinich et al. | 606/128 |
| 5,014,708 | 5/1991 | Hayashi et al. | 128/4 |
| 5,095,889 | 3/1992 | Weismuller et al. | 606/127 |
| 5,169,397 | 12/1992 | Sakashita et al. | 128/4 |
| 5,176,688 | 1/1993 | Narayan et al. | 606/128 |
| 5,190,557 | 3/1993 | Borodulin et al. | 606/128 |

*Primary Examiner*—Stephen C. Pellegrino
*Assistant Examiner*—Glenn K. Dawson
*Attorney, Agent, or Firm*—Cohen, Pontani, Lieberman, Pavane

[57] ABSTRACT

An instrument for lithotripsy having a probe which can be vibrated longitudinally by means of a drive and which extends through a guide channel in the shaft of an endoscope and is supported and guided externally of the shaft by a guide element aligned on the corresponding guide channel, is described. The guide element receives the housing of the probe drive also serving as a handle proximally, and its distal end can be releasably attached to a rinsing and probing attachment which can be connected to the proximal end of the endoscope and is provided with valves. The guide element is designed so that the valves can be actuated unimpeded.

7 Claims, 5 Drawing Sheets

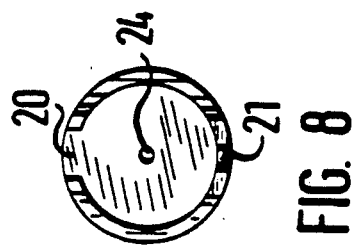
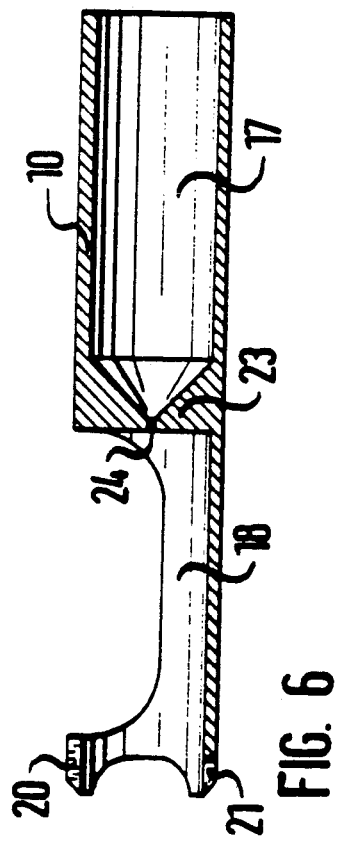
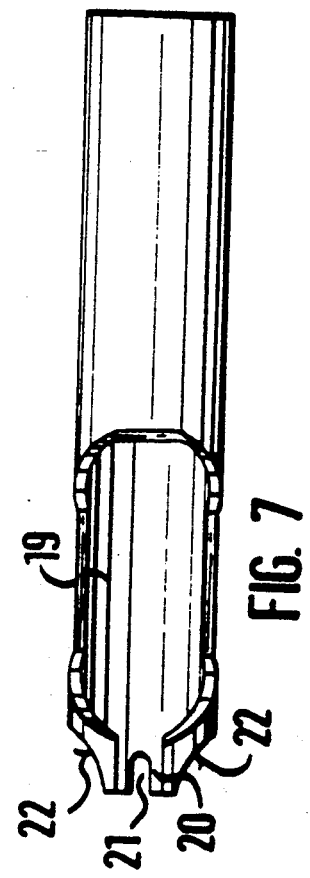

INSTRUMENT FOR LITHOTRIPSY

BACKGROUND OF THE INVENTION a) Field of the Invention

The invention relates to an instrument for lithotripsy having a probe which can be vibrated by a drive and which extends through a channel in the shaft of an endoscope and is supported and guided proximally externally of the endoscope by a guide element aligned on the channel mentioned.

b) Description of the Prior Art

In endoscopic lithotripsy ultrasound sonotrodes, pneumatic probes, lasers or EHL probes are pushed through the channel of an appropriate operation optical system provided therefor as far as the concretion. At the proximal end of these probes there is usually a relatively heavy handle part with the ultrasound transducer, the drive part of a pneumatic probe or the like.

An instrument of the type mentioned in the introduction is known, for example from German Gebrauchsmuster 77 05 947. This instrument comprises an endoscope, in which an ultrasound probe, which can be moved in the longitudinal direction by means of an ultrasound transducer, and a suction device are arranged. The ultrasound transducer is attached in a mounting forming a handpiece and which distally follows a guide element for the ultrasound probe. This handpiece can be displaced axially against spring force on guide rods by means of gripping elements which can be actuated like scissors, in order to be able to push the ultrasound probe against the concrement to be destroyed. An auxiliary instrument and a connecting unit comprising introduction valves therefor are not provided in this instrument.

The object of the invention consists in providing an instrument for lithotripsy which is simpler and lighter in construction compared to previously known instruments. Furthermore, exact guiding for rigid and semi-rigid probes should be guaranteed. Finally, it should be possible to assemble and dismantle the essential parts of the instrument simply.

SUMMARY OF THE INVENTION

This object is achieved according to the invention in that the distal end of the guide element is releasably attached to a rinsing and probing attachment connected to the endoscope and provided with valves, and has a slot extending in the proximal direction starting from its distal end and which changes into a recess, by means of which the introduction valve for the probe is accessible for the purposes of actuation, and a further valve for introducing an auxiliary instrument projects towards the outside, and in that a channel is provided in the guide element as a probe guide.

The advantages which can be achieved therewith consist particularly in the broad applicability of such an apparatus, which also permits, for example the use of a flexible probe after removing the guide element. Furthermore, this produces ease of assembly or dismantling and a stable, but nevertheless sensitively actuatable unit which can be easily cleaned and sterilised.

A preferred embodiment of the guide element allows for the fact that the handle of the introduction valve for the probe also projects through the recess towards the outside in the adapted state, so that this introduction valve can be actuated unimpeded.

A compact unit of relatively low weight and favourable centre of gravity is produced when the guide element has a substantially cylindrical shape, and proximally has a first chamber for partially receiving the housing of the probe drive and distally has a second chamber for receiving the probe introduction valve, and the guide channel for the probe is provided in a wall separating the two chambers mentioned.

In order to make simple introduction of the ultrasound probes possible during assembly, the distal end region of the first chamber mentioned in the guide element may be tapered conically in the direction of the guide channel.

In order to be able to assemble and dismantle the instrument easily, the distal end of the guide element is preferably releasably fixed to the rinsing and probing attachment by means of a screw, and the rinsing and probing attachment and the endoscope are releasably connected to one another. The ease of dismantling thus produced also makes problem-free disassembly possible for cleaning and sterilising the instrument parts.

The guide element may have cylindrical shape for secure-grip handling of the instrument and may be designed as a handle at least in the region of the part surrounding the first chamber. In addition, the housing of the drive also forms a handle.

The foregoing summary of the invention, as well as the following detailed description of the preferred embodiments, will be better understood when read in conjunction with the appended drawings. For the purposes of illustrating the invention, there are shown in the drawings embodiments which are presently preferred, it being understood, however, that the invention is not limited to the specific arrangements and instrumentalities disclosed.

FIG. 1 shows an operation endoscope with rinsing and probing attachment and guide element of the invention, FIG. 2 shows a side view of the rinsing and probing attachment, which can be adapted to an endoscope shaft, with the guide element to be attached to it, FIG. 3 shows a cross-section through the rinsing and probing attachment along the section line A-B according to FIG. 2, FIG. 4 shows a side view corresponding to FIG. 2 in the assembled state, FIG. 5 shows a side view corresponding to FIG. 4, but rotated about 90° with respect to it and shown in partial section, FIGS. 6 and 7 show a section or a view of the guide element, and FIG. 8 shows an end view of the distal end of the guide element.

DESCRIPTION OF THE PREFERRED EMBODIMENTS

Figure 1:
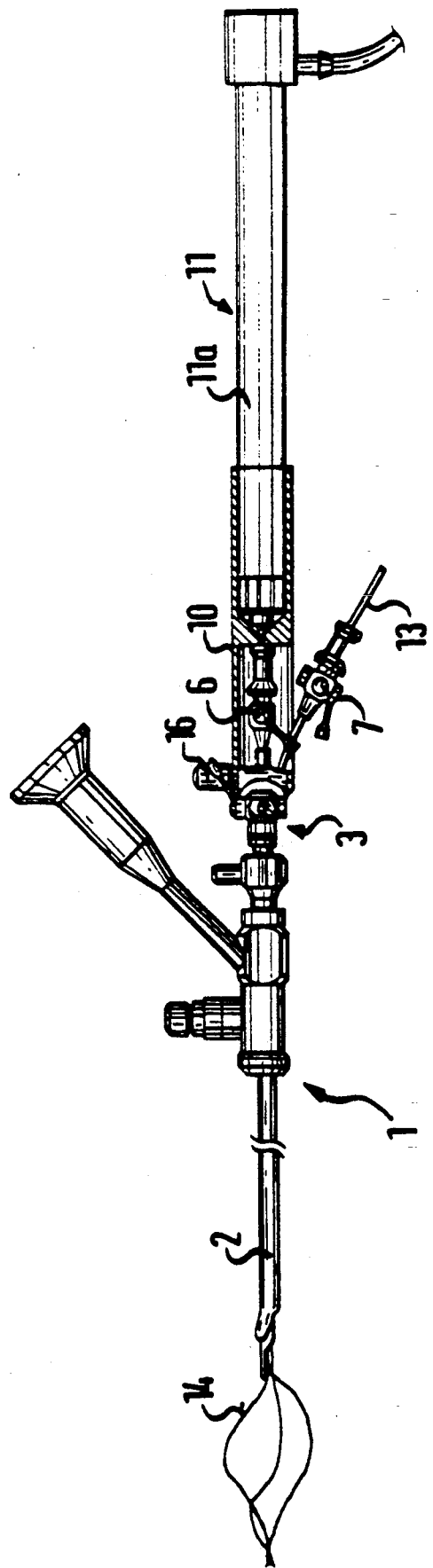
Figure 2:
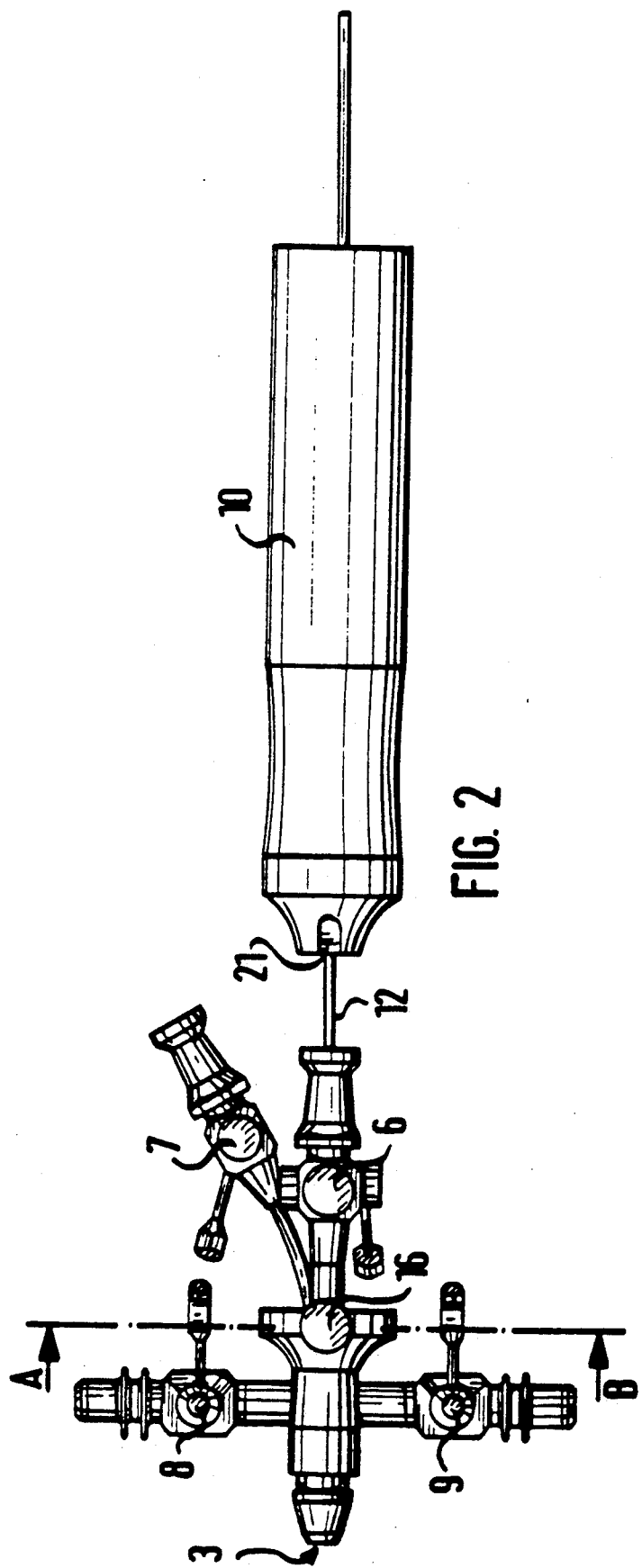
Figure 3:
Figure 4:
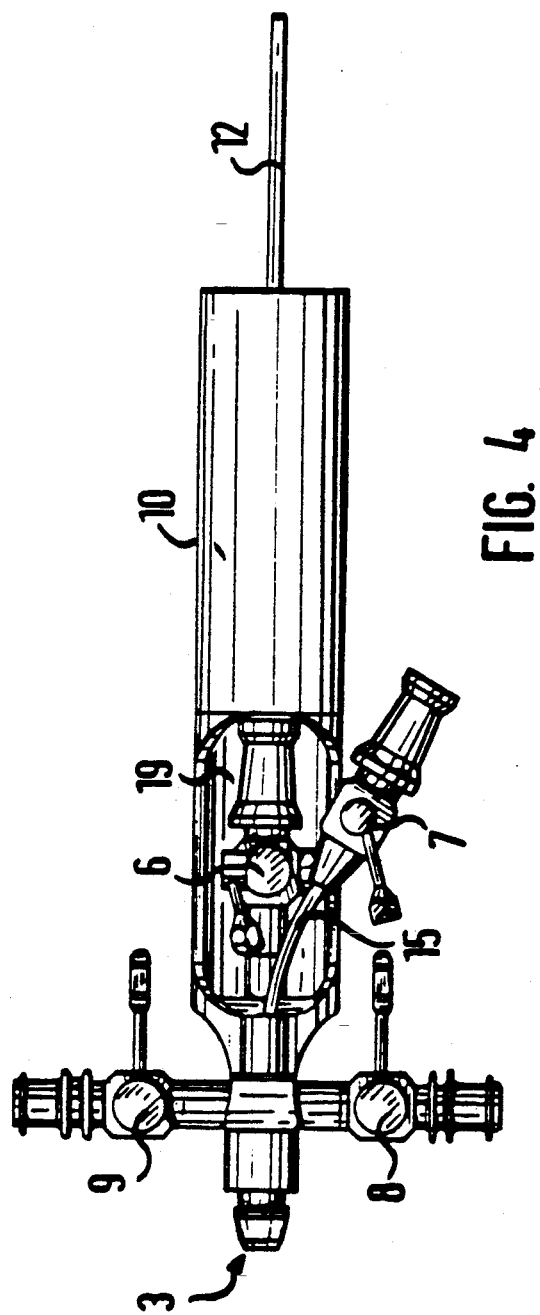
Figure 5:
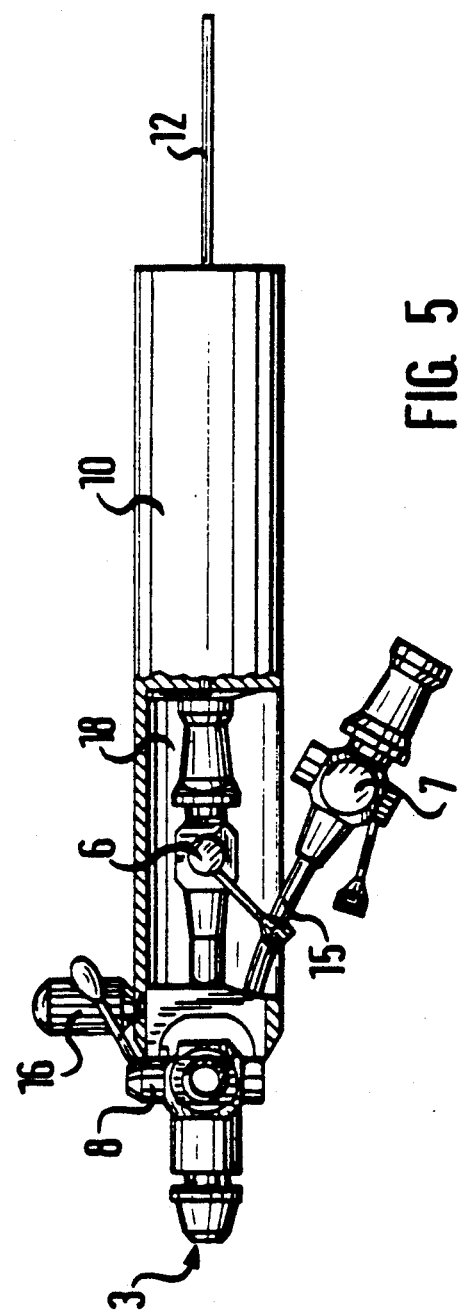

According to FIG. 1, the instrument equipped for lithotripsy comprises an endoscope 1 having a shaft 2, to the proximal end of which is attached a rinsing and probing attachment 3. This has introduction valves 6 and 7 connected with guide channels 4 and 5 (FIG. 3) of the endoscope shaft 2 and rinsing valves 8 and 9. A guide element 10 is releasably attached to the attachment 3 and its distal end partially overlaps the attachment 3, and the cylindrical housing 11a of a probe drive 11 serving as a handle is pushed into the proximal end of the guide element 10. The guide element guides an ultrasound probe 12 passing through the entire instrument proximally as far as the distal end of the endoscope shaft 2. The embodiment shown in FIG. 1 indicates an auxiliary instrument 13 with a loop 14 for fixing the concretion to be destroyed. The auxiliary instrument extends through the introduction valve 7, an introduction tube 15 and one of the channels 4, 5.

Fixing the guide element 10 to the attachment 3 takes place by means of a clamping screw 16 which is screwed in a threaded bore of the attachment 3 and the guide element 10 connects frictionally with the attachment.

The guide element 10 has a substantially cylindrical shape and on the proximal side has a first chamber 17 in the form of a cylindrical bore for receiving one end of the drive housing 11a also having a cylindrical shape, the diameters being adapted so that an easy sliding fit is produced. The guide element 10 has on the distal side a second chamber 18 which is accessible by means of a lateral recess 19. The recess 19 is open towards the distal end by means of a slot 20 as passage for the introduction tube 15 when placing the guide element 10 on the attachment 3. An open elongated hole 21 for the threaded shaft of the clamping screw 16 lies opposite this slot 20. Furthermore, the guide element 10 is provided at its distal end with grooves 22 lying laterally opposite one another to ensure free access to the actuation levers of the rinsing valves 8 and 9.

The two chambers 17 and 18 are separated from one another by a wall 23, in which a guide channel 24 is provided for the ultrasound probe 12. The distal end region of the wall 23 is thus tapered conically in the direction of the guide channel 24 to direct the ultrasound probe 12 when introducing it on the guide channel 24.

During assembly, the procedure is advantageously such that the guide element 10 is pushed over the introduction valve 6 for the ultrasound probe 12, and indeed aligned so that the introduction tube 15 may enter the slot 20. The threaded shaft of the clamping screw 16 is thus introduced into the elongated hole 21, and then the clamping screw is tightened. The introduction valve 7 for the auxiliary instrument 13 and also the lever of the introduction valve 6 for the probe 12 then project laterally from the recess 19, so that the introduction valves 6 and 7 can be actuated unimpeded. The instrument is ready for operation after pushing the ultrasound probe 12 through the guide channel 24 and the channel assigned to it in the endoscope shaft 2 and after inserting the distal end of the drive housing 11a in the chamber 17 of the guide element 10.

The instrument of the invention is intended particularly for the use of rigid or semi-rigid probes, for which exact guiding is required to avoid efficiency losses due to friction and wear in the probe guide channels. If on the other hand flexible probes are to be used, the guide element is simply removed so that the operation endoscope and the attachment as such may also be used for flexible probes.

The present invention may be embodied in other specific forms without departing from the spirit or essential attributes thereof and, accordingly, reference should be made to the appended claims rather than to the foregoing specification as indicating the scope of the invention.

What is claimed is:

1. A lithotripsy instrument, comprising: an endoscope having a shaft with a channel therein for accommodating a probe, said endoscope having a distal end and a proximal end; a rinsing and probing attachment connected to the proximal end of the endoscope, said rinsing and probing attachment having a probe introduction valve and an auxiliary instrument introduction valve; a guide element having a channel therein for guiding and supporting the probe, a proximal end and a distal end, the distal end of said guide element being releasably attached to said rinsing and probing attachment so that the channel of the guide element is aligned with the channel in the endoscope shaft, said guide element further having a slot which extends from the distal end of said guide element toward the proximal end thereof, said slot forming recess in said guide element so as to permit accessibility to and actuation of the probe introduction valve, the auxiliary instrument introduction valve being arranged to project outwardly from the recess; and, drive means for vibrating the probe.

2. An instrument according to claim 1, wherein the probe introduction valve has a handle which projects outwardly through the recess.

3. An instrument according to claim 1, wherein said drive means includes a drive housing, said guide element having a substantially cylindrical shape and proximally having a first chamber for receiving one end of the drive housing and distally having a second chamber for receiving the probe introduction valve, said first and second chambers being separated by a wall in which the guide element channel is provided.

4. An instrument according to claim 3, wherein the first chamber has a distal end region that is tapered conically in the direction of the guide channel.

5. An instrument according to claim 3, wherein said guide element is formed as a handle at least in a region of the first chamber, the drive housing also being formed as a handle.

6. An instrument according to claim 1, wherein the distal end of said guide element is fixed to said rinsing and probing attachment by a screw.

7. An instrument according to claim 1, wherein said rinsing and probing attachment and said endoscope are releasably connected to one another.

* * * * *

UNITED STATES PATENT AND TRADEMARK OFFICE
CERTIFICATE OF CORRECTION

PATENT NO. : 5,312,418
DATED : May 17, 1994
INVENTOR(S) : BONNET, Ludwig

It is certified that error appears in the above-identified patent and that said Letters Patent is hereby corrected as shown below:

On the title page item [73] Assignee;

should read as follows: Richard Wolf GmbH, A Corporation of the Federal Republic of Germany, Knittlingen, Federal Republic of Germany Signed and Sealed this Eighteenth Day of October, 1994

Attest:

BRUCE LEHMAN

*Attesting Officer*     *Commissioner of Patents and Trademarks*